(12) United States Patent
Akahoshi

(10) Patent No.: US 8,764,782 B2
(45) Date of Patent: Jul. 1, 2014

(54) PHACOEMULSIFICATION NEEDLE

(75) Inventor: Takayuki Akahoshi, Tokyo (JP)

(73) Assignee: Art, Limited, Grand Cayman (KY)

( * ) Notice: Subject to any disclaimer, the term of this patent is extended or adjusted under 35 U.S.C. 154(b) by 1 day.

(21) Appl. No.: 12/404,307

(22) Filed: Mar. 15, 2009

(65) Prior Publication Data
US 2011/0015561 A1    Jan. 20, 2011

Related U.S. Application Data

(63) Continuation-in-part of application No. 12/263,315, filed on Oct. 31, 2008.

(60) Provisional application No. 61/150,320, filed on Feb. 6, 2009.

(51) Int. Cl.
*A61B 17/3205* (2006.01)
*A61F 9/007* (2006.01)
*A61B 17/32* (2006.01)

(52) U.S. Cl.
CPC . *A61F 9/00745* (2013.01); *A61B 2017/320096* (2013.01); *A61B 2017/320072* (2013.01)
USPC .............................. 606/169; 606/171; 604/22

(58) Field of Classification Search
CPC ............... A61F 9/00745; A61B 2017/320072; A61B 2017/320096
USPC ................. 606/107, 166, 167, 169, 170, 171; 604/22, 25, 44, 264, 272, 275, 289, 604/290, 294
See application file for complete search history.

(56) References Cited

U.S. PATENT DOCUMENTS

| | | | | |
|---|---|---|---|---|
| 2,830,587 A * | 4/1958 | Everett | ......................... | 604/272 |
| 4,515,583 A * | 5/1985 | Sorich | ............................ | 604/22 |
| 4,825,865 A * | 5/1989 | Zelman | ........................... | 606/6 |
| 4,869,259 A * | 9/1989 | Elkins | .......................... | 600/458 |
| 5,112,339 A * | 5/1992 | Zelman | ........................ | 606/107 |
| 5,478,328 A * | 12/1995 | Silverman et al. | ............ | 604/272 |
| 5,645,537 A * | 7/1997 | Powles et al. | ................. | 604/240 |
| 6,110,128 A * | 8/2000 | Andelin et al. | ............... | 600/566 |
| 6,165,150 A * | 12/2000 | Banko | ............................. | 604/22 |
| 2004/0267211 A1 * | 12/2004 | Akahoshi | ...................... | 604/264 |
| 2006/0052758 A1 * | 3/2006 | Dewey | .......................... | 604/272 |
| 2008/0294087 A1 * | 11/2008 | Steen et al. | ..................... | 604/22 |

* cited by examiner

*Primary Examiner* — Kathleen Holwerda
(74) *Attorney, Agent, or Firm* — Wood, Phillips, Katz, Clark & Mortimer

(57) ABSTRACT

A phacoemulsification needle having a hollow passageway terminates in a straight needle tip formed off-axis from the passageway, allowing the needle tip to move eccentrically when the needle is subjected to torsional or longitudinal vibratory motion. The tip may be flared or may be coextensive with the needle body. The aspiration passageway formed through the needle body may be formed off-axis from the needle body axis. The tip may also be angled with respect to the needle body. The inner and outer surfaces of the needle tip are roughened, as by sandblasting, to enhance the cutting effect of the tip when used with a non-longitudinal handpiece. The lip of each needle tip is polished to a high degree of smoothness and the edges of the tip are rounded to lessen the incidence of snags or cuts.

20 Claims, 8 Drawing Sheets

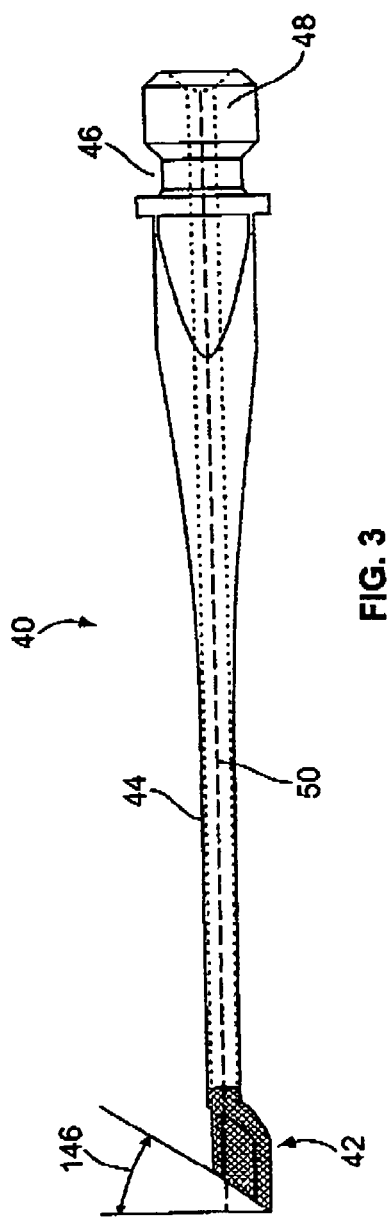
FIG. 3
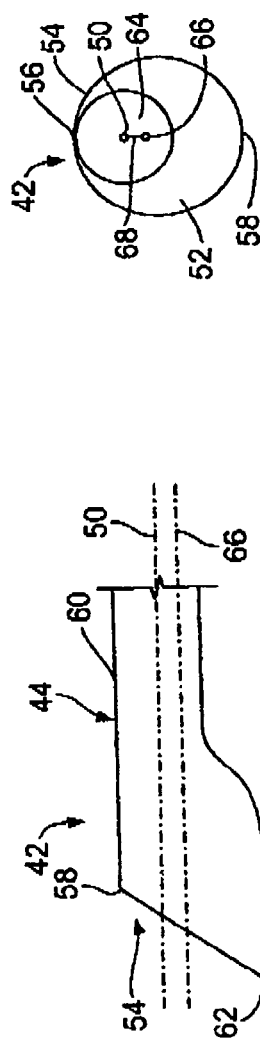
FIG. 5
FIG. 4

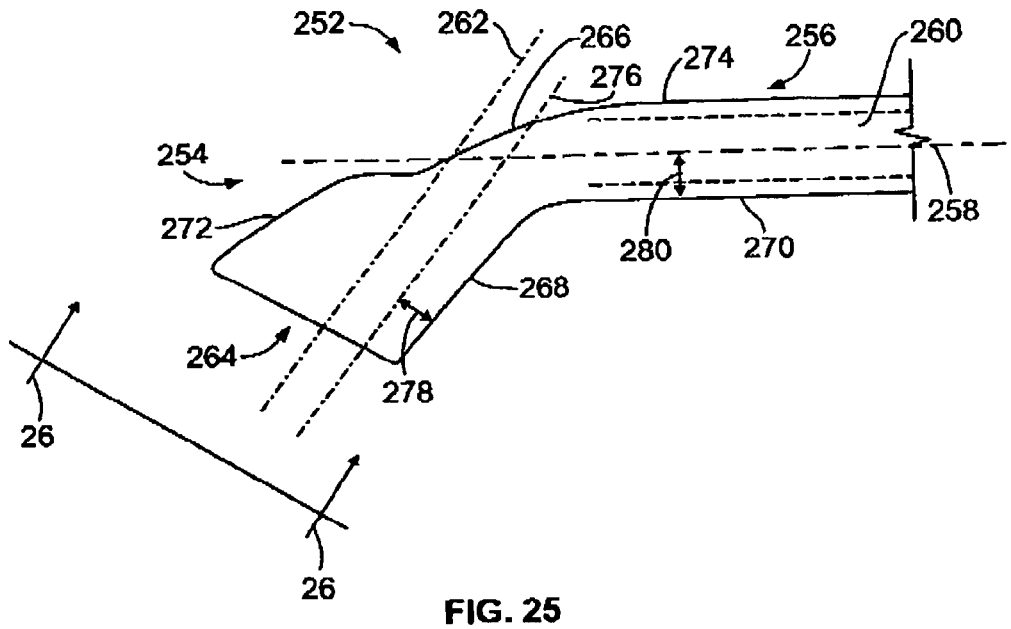
FIG. 25
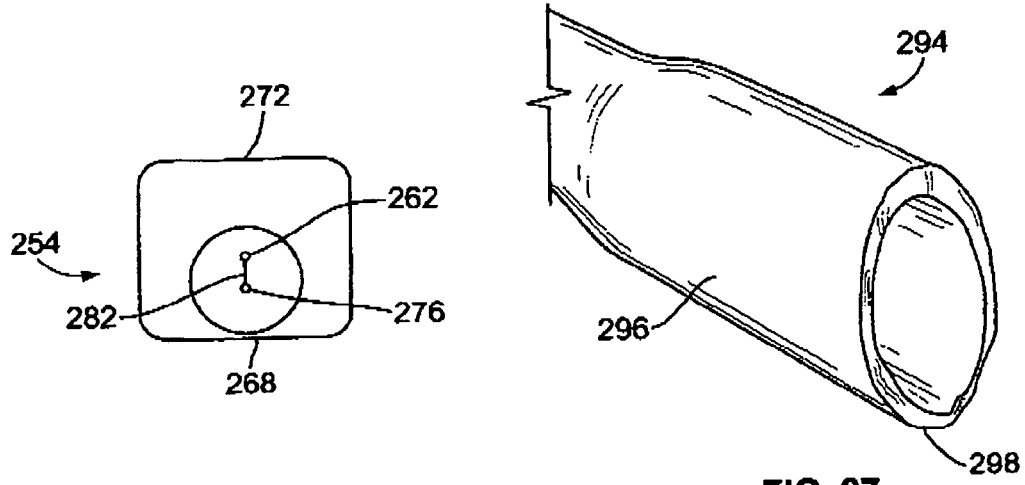
FIG. 26
FIG. 27

PHACOEMULSIFICATION NEEDLE

This application is a continuation-in-part of U.S. patent application Ser. No. 12/263,315, filed 31 Oct. 2008, and claims priority from U.S. Provisional Patent Application Ser. No. 61/150,320, filed 6 Feb. 2009, both of which are incorporated herein in their entirety by reference.

FIELD OF THE INVENTION

This disclosure relates to surgical instruments and surgical techniques used in eye surgery and more particularly, to phacoemulsification apparatus and methods for their use.

BACKGROUND OF THE INVENTION

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such removal technique is known as phacoemulsification. A typical phacoemulsification tool includes a handpiece to which is attached a hollow needle. Electrical energy is applied to vibrate the needle at ultrasonic frequencies in order to fragment the diseased lens into small enough particles to be aspirated from the eye through the hollow needle. Commonly, an infusion sleeve is mounted around the needle to supply irrigating liquids to the eye in order to aid in flushing and aspirating the lens particles.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage is permanent because these cells do not regenerate. One of the benefits of using as small in incision as possible during such surgery is the minimization of leakage of liquid during and after surgery and the prevention of such a collapse.

Phacoemulsification needles and tips are well represented in the prior art. Needles and tips of varying configurations are well known. A particular shape for a tip or needle is often dictated by the type of handpiece with which the needle is to be used.

U.S. Pat. No. 5,725,495 (Strukel et al) teaches and describes a phacoemulsification handpiece, sleeve and tip illustrating a wide variety of tip configurations and needle cross-sectional configurations.

U.S. Pat. No. 6,007,555 (Devine) teaches and describes an ultrasonic needle for surgical emulsification. The needle and its tip are shown in both circular and oval configurations.

U.S. Pat. No. 6,605,054 (Rockley) teaches and describes a multiple bypass port phacoemulsification tip having multiple aspiration ports and a single discharge port to infuse liquid into the eye.

U.S. Pat. No. 5,879,356 (Geuder) teaches and describes a surgical instrument for crushing crystalline eye lenses by means of ultrasound and for removing lens debris by suction which demonstrates the use of a sleeve positioned concentric to the needle and having a pair of discharge ports formed thereon.

U.S. Pat. No. 5,645,530 (Boukhny) teaches and describes a phacoemulsification sleeve, one variation of which has a bellows portion attached to a discharge port ring which directs an annular flow of liquid around the needle and into the eye. The use of the bellows is intended to allow the sleeve to absorb spikes in liquid pressure during the operation.

Published U.S. Patent Application No. 2003/0004455 (Kadziauskas) teaches and describes a bi-manual phacoemulsification needle using separate emulsification and aspiration needles inserted into the eye simultaneously during surgery.

Published U.S. Patent Application No. 2006/0217672 (Chon) teaches and describes a phacoemulsification tip that is swaged or crimped at its distal end. The tip is intended for use with a handpiece producing torsional motion and the crimping forms cutting edges at the distal end.

Many phacoemulsification needles and tips are designed for use with handpieces that vibrate the needle longitudinally at relatively low frequencies. In addition to longitudinal vibration, the NeoSoniX® handpiece sold by Alcon, Inc. of Ft. Worth, Tex. has a rotational or torsional oscillation vibration frequency of about 100 cycles/second. There are also handpieces that provide torsional oscillation of the phacoemulsification tip at frequencies of about 32,000 cycles/second.

Use of the torsional-type handpiece has called for phacoemulsification needle tip designs differing from those used with the longitudinal-type handpiece. For example, needles have been designed with tips that are shaped, swaged and angled to take advantage of the torsional motion created by the handpiece.

Many surgeons favor phacoemulsification needles having the straight tip design most commonly used with longitudinal handpieces but have found that using them with torsional handpieces does not produce good results.

I have found that forming the needle tip in an off-axis position relative to the axis of the needle body causes sufficient eccentric motion, or "wobble" during torsional motion to produce improved phacoemulsification results while retaining the straight-tip configuration. Forming the needle body in an asymmetric configuration also produces useful "wobble". I have also determined that use of an off-axis needle tip or needle body improves performance when the needle is used in a non-longitudinal type of handpiece, such as in the torsional mode or the elliptical mode.

In accordance with a preferred embodiment of the apparatus a phacoemulsification needle is provided for use with a high-frequency torsional phacoemulsification handpiece with the needle having a straight needle tip with the tip being formed off-axis with respect to the hollow passage formed through the needle.

In accordance with another preferred embodiment, the needle body is formed with an off-axis central aspiration passageway, a central aspiration passageway with a cross-sectional shape different from that of the needle body, or a combination of these configurations, and combined with a standard or an off-axis needle tip.

While the following describes a preferred embodiment or embodiments of the present invention, it is to be understood that such description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

BRIEF DESCRIPTION OF THE DRAWINGS

Further aspects of the present invention will be best understood by reference to the accompanying drawings in which like numbers are used to identify like parts, and which are presented to illustrate the aspects of the invention although not necessarily to actual scale, wherein:

FIG. 3 is a lateral schematic view of a phacoemulsification needle embodying the present invention;

FIG. 4 is a partial lateral view of the needle tip of FIG. 3;

FIG. 5 is a view taken along 5-5 of FIG. 4;

FIG. 25 is a lateral view of a phacoemulsification needle with an angled tip formed off-axis to the needle body;

FIG. 26 is a view along 26-26 of FIG. 25;

FIG. 27 is an enlarged view of a flared phacoemulsification needle tip;

DETAILED DESCRIPTION OF THE INVENTION

Figure 1:
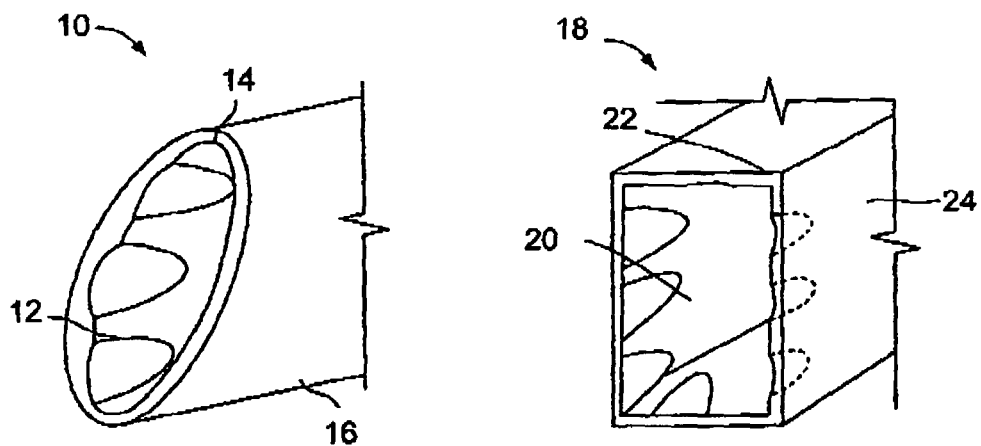
FIG. 1 is a drawing showing prior art straight oval- and square-shaped tips.

Referring now to FIG. 1, the numeral 10 indicates generally a prior art phacoemulsification needle tip as shown in U.S. Pat. No. 6,007,555. Needle 10 terminates in a mouth 12 defined by a lip 14 at the end of needle body 16, with lip 14 and needle body 16 formed as having an oval cross-section configuration.

Referring to FIG. 1, the numeral 18 indicates generally a prior art phacoemulsification needle tip from U.S. Pat. No. 6,007,555, having a mouth 20 defined by a lip 22 at the end of needle 24. The cross-sectional configuration of needle 18 and mouth 20 is a rectangle.

Figure 2:
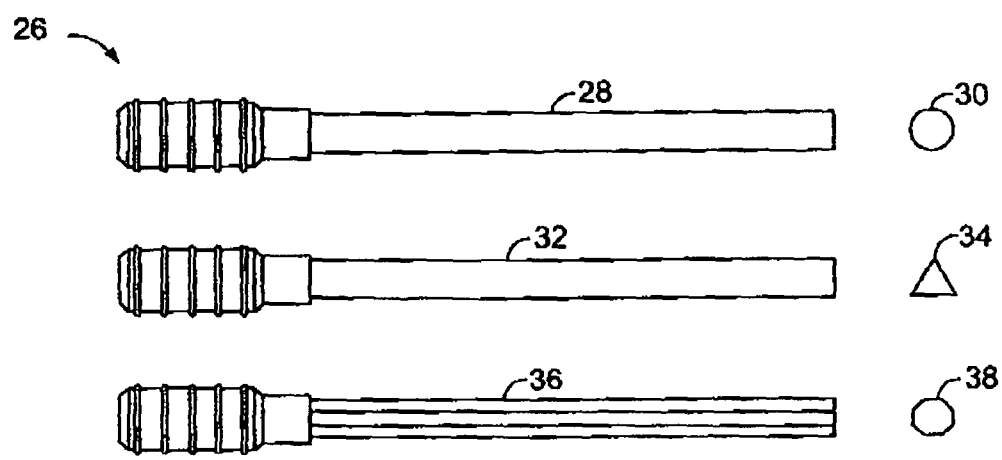
FIG. 2 is a drawing showing several prior art needle cross-sectional configurations.

Referring now to FIG. 2, the numeral 26 identifies several prior art phacoemulsification needles as described in U.S. Pat. No. 5,725,495, with needle 28 having a circular cross-section as shown at 30, needle 32 having a triangular cross-section as shown at 34 and needle 36 having an octagonal cross-section as shown at 38.

Both tips 10 and 18 in FIG. 1 exemplify one form of a "straight" needle tip, that is, a tip that is coaxial with or centered on the hollow aspiration passageway formed through the needle body. Other straight tips are known which have needle tips that are flared, that is, larger in cross-sectional area than the needle's aspiration passageway yet which are centered on the passageway.

Referring now to FIG. 3, the numeral 40 indicates generally a phacoemulsification needle embodying certain aspects of the present invention. Needle 40 has a needle tip 42 formed integrally with a hollow needle body 44 at a distal end thereof. At a proximal end thereof, needle body 44 has a needle end 46 which terminates in a mount 48 which allows needle 40 to be attached to a phacoemulsification handpiece. In the example shown, needle body 44 has a circular cross-section with a longitudinally-extending central axis 50.

Referring to FIG. 4, an enlarged detail of tip 42 is shown. As seen in both FIGS. 4 and 5, tip 42 has a mouth 52 defined by a lip 54 which, in the example shown in FIGS. 3 and 4, is formed at a 30° angle 146 to axis 50. The angle shown is one of choice: lip 54 can also be formed perpendicular to axis 50 or any number of other configurations corresponding generally to the configurations of known straight tips presently used with longitudinally-vibrating hand pieces.

As viewed in FIG. 4, tip 42 has a lead portion 56 and a trailing portion 58, with lead portion 56 being that part of lip 54 that extends longitudinally forward past trailing portion 58, while trailing portion 58 is that part of lip 54 that extends the least distance forward. In the example shown in FIG. 4, trailing portion 58 is substantially coextensive with the outer surface 60 of needle body 44, while lead portion 56 is offset by a distance 62 from the outer surface 60 of needle body 44. The effect of forming lip 54 at the angle shown is to place lead portion 56 at the farthest point from needle body axis 50.

Referring now to FIG. 5, the aspiration passageway 64 of needle body 44 is shown to illustrate the position of axis 50. Tip mouth 52 is shown defined by lip 54 with lead point 56 and trailing point 58. In the example shown, tip 42 has a circular cross-section having its own central tip axis 66 extending therethrough. As seen in FIGS. 4 and 5, in this example, axes 50 and 66 do not coincide but are offset by a distance 68. As also seen in FIG. 5, the cross-sectional area of tip 42 is larger than the cross-sectional area of needle body 44 when viewed in a plane perpendicular to axis 50.

In a preferred example needle body 44 is 1.0 mm in exterior diameter with a wall thickness of 0.10 mm, leaving an interior diameter of 0.80 mm. Tip 42 has an exterior diameter of 1.10 mm and a wall thickness of 0.10 mm. The lateral distance from the point at which tip 42 begins to enlarge outward from needle body 44 to lead point 56 is 1.80 mm, while offset distance 62 is 0.30 mm.

Figure 6:
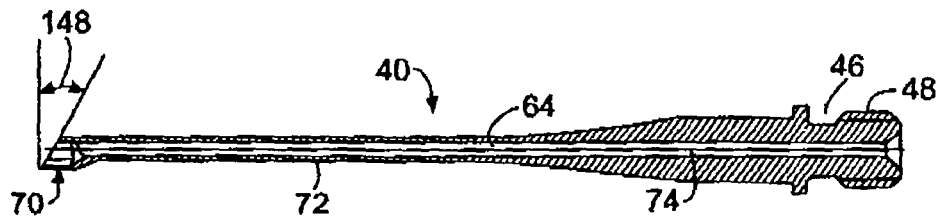
FIG. 6 is a lateral schematic view of a second phacoemulsification needle embodying the present invention.

Referring now to FIG. 6, a second example of a needle tip formed on needle 40 is shown, embodying certain aspects of the present invention. Needle tip 70 is square in cross-sectional shape and is formed integrally with a hollow needle body 72. In the example shown, needle body 72 has a circular cross-section with a longitudinally-extending central axis 74.

Figure 7:
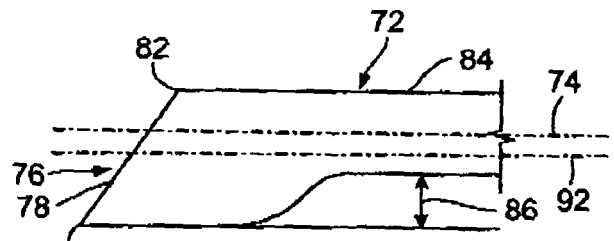
FIG. 7 is a lateral view the needle tip of FIG. 6.

Referring to FIG. 7, an enlarged detail of tip 70 is shown. As seen in both FIGS. 7 and 8, tip 70 has a mouth 76 defined by a lip 78 which, in the example shown in FIGS. 6 and 7, is formed at a 30° angle 148 to axis 74. The angle shown is one of choice: lip 78 can also be formed perpendicular to axis 74 or any number of other configurations corresponding generally to the configurations of known straight tips presently used with longitudinally-vibrating hand pieces.

As viewed in FIG. 7, tip 70 has a lead lip portion 80 and a trailing lip portion 82, with lead portion 80 being that part of lip 78 that extends longitudinally past trailing portion 82, while trailing portion 82 is that part of lip 78 that extends the least distance longitudinally forward. In the example shown in FIG. 7, trailing lip portion 82 is substantially coextensive with the outer surface 84 of needle body 72, while lead lip portion 80 is offset by a distance 86 from the outer surface 84 of needle body 72. The effect of forming lip 78 at angle 148 is to place lead lip portion 80 farthest from needle body axis 94.

Figure 8:
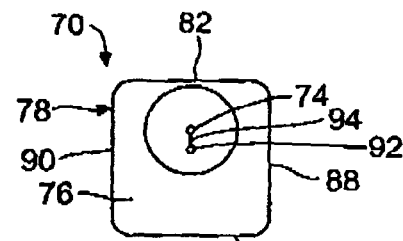
FIG. 8 is a view taken along 8-8 of FIG. 6.

Referring now to FIG. 8, the aspiration passageway 64 of needle body 72 is shown, with central axis 74. Mouth 76, defined by lip 78, has a first slanted lip portion 88 extending from lead point 80 to trailing point 82, and a second slanted lip portion 90 disposed opposite lip portion 88 and also extending from lead portion 80 to trailing portion 82. In the example shown, tip 70 has a square cross-section having its own central axis 92, which, as seen in FIGS. 7 and 8 is offset from needle body axis 74 by a distance 94. As also seen in FIG. 8, the cross-sectional area of tip 70 is greater than the cross-sectional area of needle body 72 when viewed in a plane perpendicular to axis 74.

Figure 9:
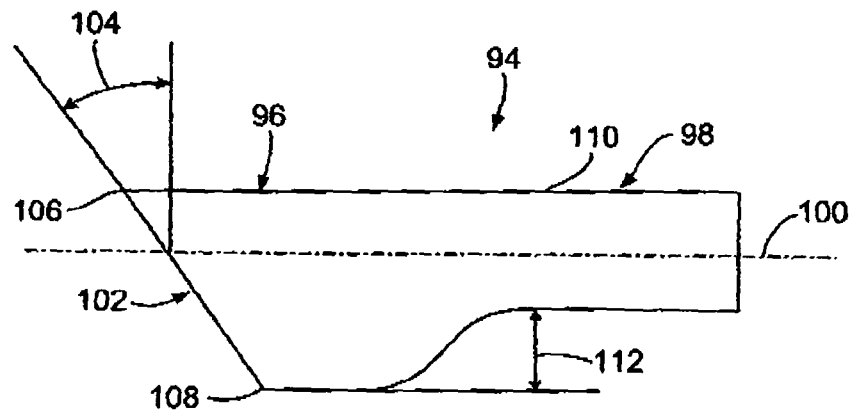
FIG. 9 is a partial lateral view of a variation of the tip shown in FIG. 3.

Referring now to FIG. 9 the numeral 94 identifies a phacoemulsification needle constructed substantially as described with respect to FIGS. 3, 4 and 5. Needle 94 has a tip 96 formed with a circular cross-section and integral with needle body 98. Needle body 98 has a central axis 100.

Tip 96 has a circular mouth 102 which, in this example, is formed at an angle 104 to axis 100. In this example, angle 104 is measured 30° in a direction opposite to that of angle 146 of mouth 52 as shown in FIG. 4. In this configuration, tip 96 has a lead point 106 and a trailing point 108, corresponding in description to points 56, 58 described above. In this example, lead point 106 is coextensive with outer surface 110 of needle body 98 while trailing point 108 is offset from outer surface 110 by a distance 112.

Figure 10:
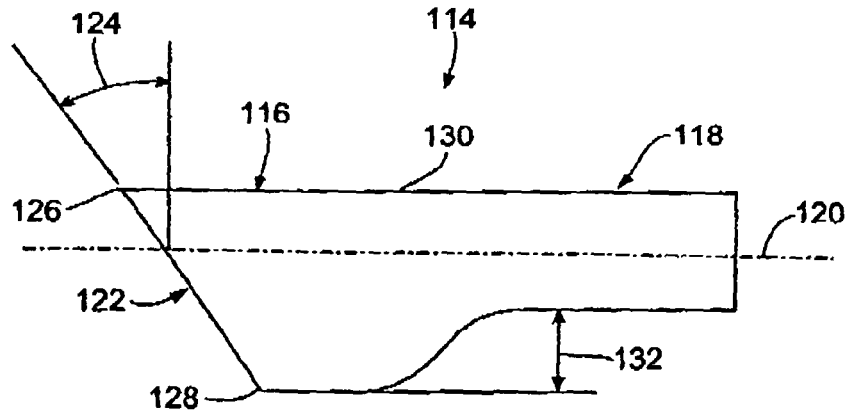
FIG. 10 is a partial lateral view of a variation of the tip shown in FIG. 6.

Referring now to FIG. 10 the numeral 114 identifies a phacoemulsification needle constructed substantially as described with respect to FIGS. 6, 7 and 8. Needle 114 has a tip 116 formed with a square cross-section and integral with needle body 118. Needle body 118 has a central axis 120.

Tip 116 has a square mouth 122 which, in this example, is formed at an angle 124 to axis 120. In this example, angle 124 is measured 30° in a direction opposite to that of angle 148 of mouth 74 as shown in FIG. 6. In this configuration, tip 114 has a lead lip portion 126 and a trailing lip portion 128, corresponding in description to lip portions 78, 80 described above. In this example, lead lip portion 126 includes a portion of outer surface 130 of needle body 118 while trailing lip portion 128 is offset from outer surface 110 by a distance 132.

Figure 11:
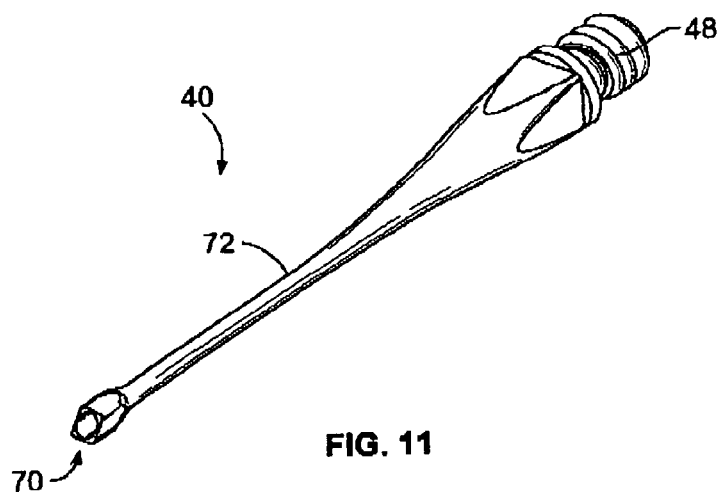
FIG. 11 is an illustration of the end of a prior art straight needle tip during torsional motion.
Figure 12:
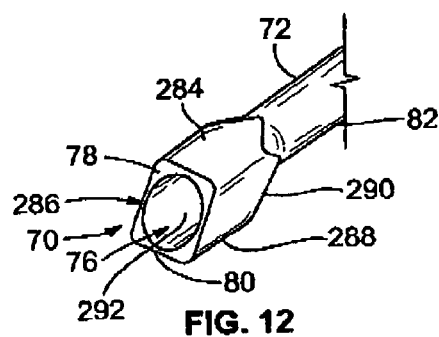
FIG. 12 is an illustration of the end of a needle tip constructed in accordance with the present invention and used with torsional motion.
Figure 13:
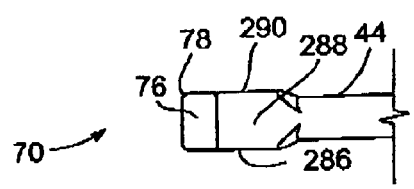
FIG. 13 is a bottom view of FIG. 12.

Referring now to FIG. 11, a perspective view of needle 40 is shown, as described above in connection with FIGS. 6, 7 and 8. Needle 40 has needle body 72 terminating at one end at tip 70 and at the other end at threaded mount 48. FIG. 12 is an enlarged perspective view of tip 70 showing the square configuration of mouth 76, lip 78 and leading and trailing portions 80, 82. FIG. 13 is a bottom view of tip 70 showing mouth 76, lip 78 and needle body 72.

Figure 14:
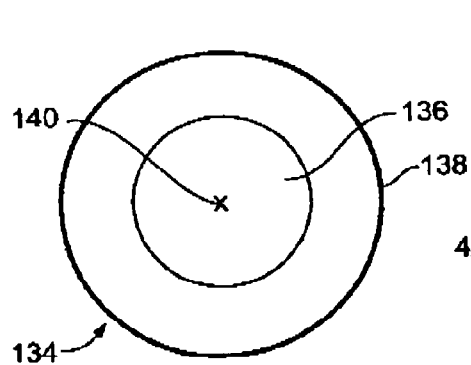
FIG. 14 is an illustration of the end of a prior art straight needle tip during torsional motion.
Figure 15:
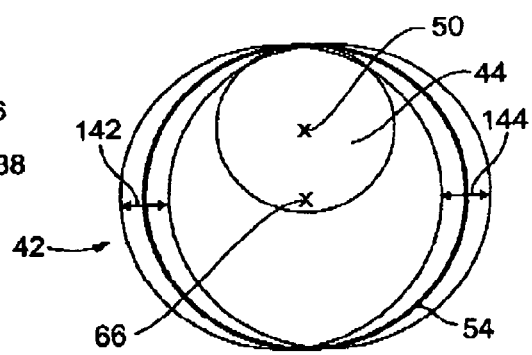
FIG. 15 is an illustration of the end of a needle tip constructed in accordance with the present invention and used with torsional motion.

The efficacy of having the tip axes in each of the foregoing examples be non-coincident with, or offset from, the needle body axes is demonstrated in FIGS. 14 and 15. Using a circular tip as an example, the numeral 134 in FIG. 14 identifies a prior art straight phacoemulsification tip having a circular cross-section defined by mouth 136 integral with and centered on needle body aspiration passageway 138. Needle passageway 138 has a central, longitudinally-extending axis 140. The geometry of tip 134 is such that axis 140 is also a central, longitudinally-extending axis for tip 134. When needle body 138 with tip 134 is attached to a phacoemulsification handpiece that produces torsional motion about axis 140 the pattern of vibration exhibits little side-to-side or eccentric motion. In other words, lip 136 tends to rotate in a generally uniform motion about axis 140.

Referring now to FIG. 15, tip 42 of FIG. 5 is shown, with circular lip 54 and needle body passageway 44 having needle body axis 50 and tip axis 66. When tip 42 is subjected to torsional rotation about axis 50 lip 54 moves eccentrically, or "wobbles" as it rotates, in part because tip 42's rotation is not centered on tip axis 66. This produces movement of lip 54 shown by paths 142 and 144, creating an enhanced cutting or emulsifying effect on the tissue contacted by tip 42. Thus, a straight phacoemulsification needle and tip can be used with a torsional phacoemulsification handpiece.

The "wobble" effect can be altered by changing the offset distance between the tip axis and the needle body axis, and by changing the geometry of the tip, by using different cross-sectional shapes such as triangular or polygonal.

Figure 16:
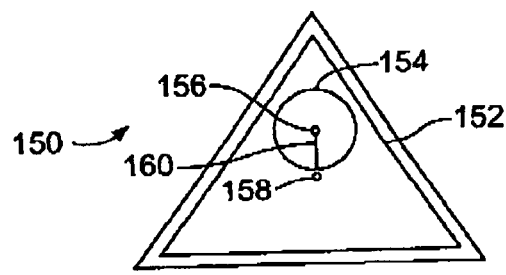
FIG. 16 is an end view showing a needle having a triangular offset tip.

Referring now to FIG. 16, the numeral 150 identifies a phacoemulsification tip having a triangular cross-sectional configuration terminating at a lip 152 and communicating with a needle aspiration passageway 154 having an axis 156. Tip 150 has a central tip axis 158 offset from axis 156 by an offset distance 160.

Figure 17:
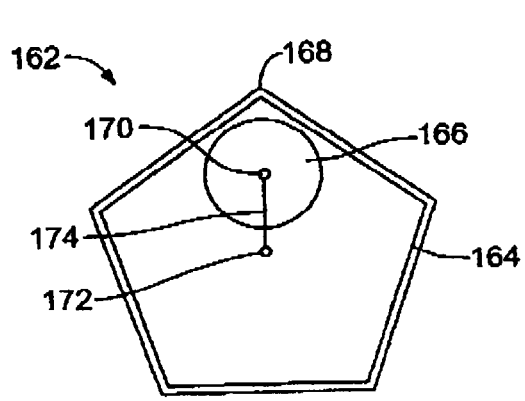
FIG. 17 is an end view of a needle having a pentagonal offset tip with the aspiration passageway formed at an apex to adjacent sides of the pentagon.

Referring now to FIG. 17, the numeral 162 identifies a phacoemulsification tip having a pentagonal cross-section terminating at a lip 164. Tip 162 communicates with a needle aspiration passageway 166 proximate apex 168. Passageway 166 has a central axis 170 and tip 162 has a central axis 172 offset from axis 170 by an offset distance 174.

Figure 18:
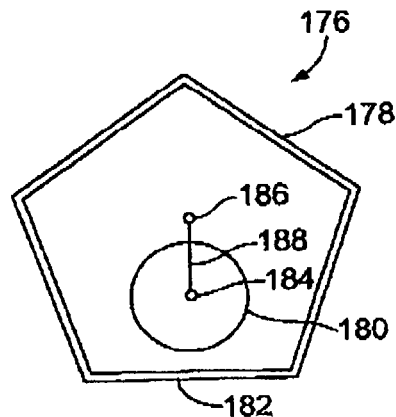
FIG. 18 is a view of FIG. 17 showing the aspiration passageway positioned along one side of the pentagonal tip.

Referring now to FIG. 18, the numeral 176 identifies a phacoemulsification tip having a pentagonal cross-sectional shape terminating in a lip 178. A needle aspiration passageway 180 extends to tip 176 proximate tip wall 182. Passageway 180 has a central axis 184 while tip 176 has a central axis 186 offset from axis 184 by offset distance 188.

Figure 19:
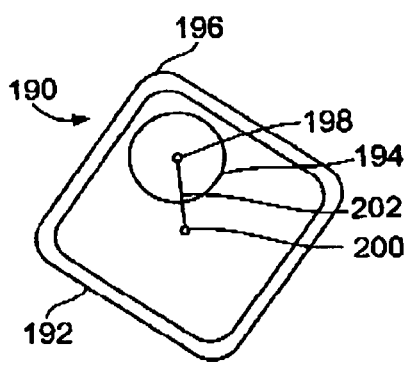
FIG. 19 is an end view of a square tip showing the aspiration passageway positioned at an apex of two adjacent sides of the square.

Referring now to FIG. 19, the numeral 190 identifies a phacoemulsification tip having a square cross-sectional shape terminating in a lip 192. A needle aspiration passageway 194 extends to and joins tip 190 proximate apex 196 of lip 192. Passageway 194 has a central axis 198 while tip 190 has a central axis 200 offset from axis 198 by an offset distance 202.

Phacoemulsification tips embodying the principles of the present invention may also be formed on needle bodies that are non-circular in cross-section.

Figure 20:
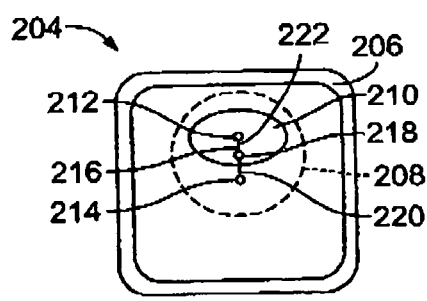
FIG. 20 is an end view of a square tip extending from a needle body having a circular outer cross-section and an aspiration passageway with an oval cross-section.

Referring now to FIG. 20, the numeral 204 identifies a phacoemulsification tip having a square cross-sectional shape terminating in a lip 206. Tip 204 extends from a needle body 208 having a circular cross-sectional shape. Needle body 208 has an oval-shaped needle aspiration passage 210 having a central axis 212 while tip 204 has a central axis 214 offset from axis 212 by an offset distance 216.

As seen in FIG. 20, needle body 208 has an axis 218 that is geometrically centered even though the distribution of the metal forming the needle is not uniform about axis 218. Axis 218 is offset from tip axis 214 by an axis offset 220 and is offset from aspiration passageway axis 212 by offset 222. The degree to which tip 204 will wobble will be affected by the choice of selected offsets 216, 220 and 222.

The foregoing examples have shown tips with flared shapes, that is cross-sectional shapes that are larger in size than the cross sectional shape of the needle body. Certain principles of the present invention are also effective for phacoemulsification needles with no flared tip that is the terminus of the needle is the same cross-sectional shape as the needle body.

Figure 21:
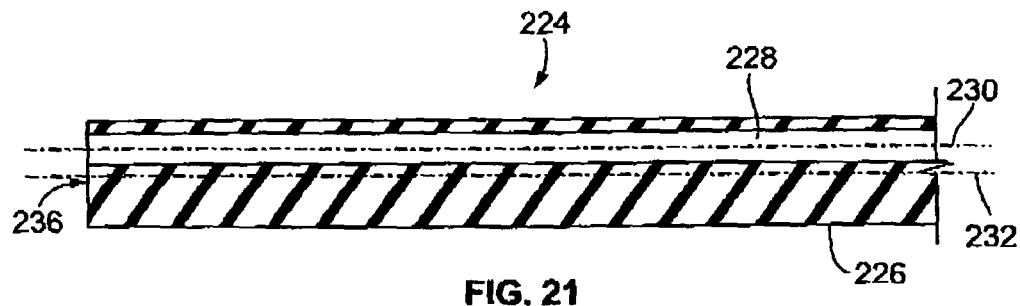
FIG. 21 is a lateral sectional view of a portion of a straight, unflared phacoemulsification needle having a circular exterior cross-section shape and an internal aspiration passageway having an oval cross-sectional shape.
Figure 22:
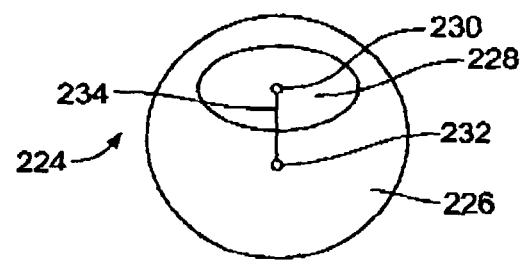
FIG. 22 is an end view of the needle of FIG. 21.

Referring now to FIG. 21, the numeral 224 identifies a straight phacoemulsification needle having a needle body 226 through which an aspiration passageway 228 is formed. As shown in FIG. 22, passageway 228 has an oval cross-sectional shape and has a central axis 230. Needle body 226 has a central axis 232 offset from passageway axis 230 by an offset distance 234. Needle 224 terminates at an unflared tip 236.

Figure 23:
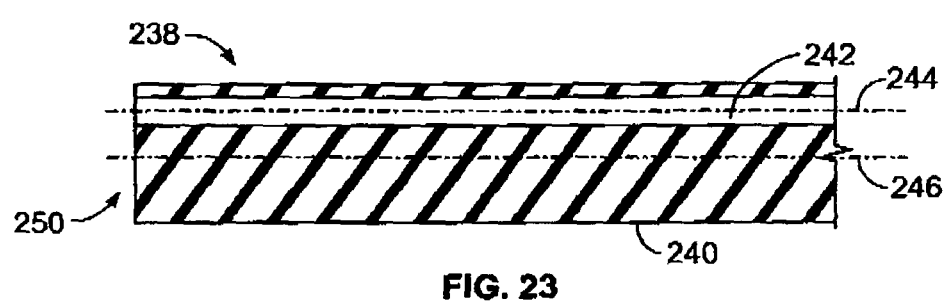
FIG. 23 is a lateral sectional view of a portion of a straight, unflared phacoemulsification needle having an oval cross-sectional shape with an aspiration passageway having a circular cross-sectional shape and offset toward one end of the needle body.
Figure 24:
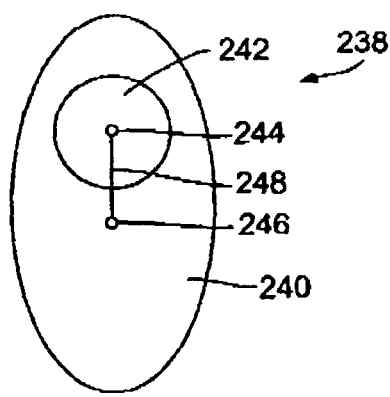
FIG. 24 is an end view of the needle of FIG. 23.

Referring now to FIG. 23, a straight phacoemulsification needle 238 has a needle body 240 formed with an oval cross-section. As shown in FIG. 24 an aspiration passageway 242 is formed through needle body 240 and in the embodiment shown has a circular cross-section. Passageway 242 has a central axis 244 and needle body 240 has a central axis 246 offset from axis 244 by an offset distance 248. Needle 238 terminates at an unflared tip 250.

I have also determined that offsetting the tip of an angled phacoemulsification needle tip increases efficiency as compared to a symmetrically fashioned tip. Phacoemulsification needles having flared tips that are angled with respect to the needle body are known in the art. Heretofore, such tips have been formed such that the bent portion of the needle body met the flared tip such that the tip was symmetrical about the needle body.

Referring now to FIG. 25 the numeral 252 identifies a portion of a phacoemulsification needle which includes a flared tip 254 and a needle body 256. Needle body 256 has a longitudinal axis 258 and an aspiration passageway 260 extending along its length. Tip 254 has an axis 262 that is centered on the tip opening 264. In this example, the tip has a square cross-section as best seen in FIG. 26.

A bend 266 is formed on needle body 256 and, as shown in FIG. 25, tip 254 is formed with a first wall portion 268 that is coextensive with bend 266 and first needle body portion 270. Tip 254 has a second wall portion 272 that is offset from bend 266 and needle body portion 274. Secondary needle body axis 276 is shown as positioned the same distance 278 from first wall portion 268 as the distance 280 axis 258 is positioned from first needle body portion 270.

Referring now to FIG. 26, an end view of tip 254 is shown takes as a view perpendicular to line 26-26 of FIG. 25. Axes 262 and 278 are shown to offset one from the other by a distance 282. This offset increases the eccentric motion exhibited by tip 254 and makes phacoemulsification more efficient.

The safety and efficiency of phacoemulsification tips embodying the foregoing aspects of the present invention are enhanced when the inner and outer surfaces of the phacoemulsification tip is roughened, as by sandblasting, and where the lip of the tip mouth is polished to round the lip and remove burrs which can damage delicate tissue in the eye, such as the posterior capsule, which may be contacted by the needle tip during phaco.

The square tip 70 shown in FIGS. 11, 12 and 13 is exemplary of the type of surfaces to which the roughening process is applied.

As seen in FIG. 12, tip 70 has an upper face 284, a left lateral face 286, a lower face 288 and a right lateral face 290. The identifiers "left" and "right" are used here to designate those faces as seen by one viewing FIG. 12. As can be appreciated, tip 70 has four external faces, all of which are roughened, beginning at and extending away from lip 78.

As further seen in FIG. 12, tip 70 has an inner tip surface 292 extending rearward toward needle body 72 and aspiration passageway 64. It is a feature of the present invention that the inner tip surface 292 is also roughened, as by sandblasting. The inner and outer surfaces of tip 70 are modified by roughening to create an uneven geometry providing numerous projections which are engaged by the tissue being emulsified as tip 70 is driven in its eccentric, or "wobble" motion.

It is another feature of the present invention to enhance the safety of the tips described herein by highly polishing the lip of each. Referring to FIG. 27 the numeral 294 identifies a phacoemulsification needle having a flared tip 296 terminating at a lip 298. In the example shown, tip 296 has a circular cross-section but the following description applies to the various tips of varying geometry described herein. Tip 296 is intended to be representative of phacoemulsification tips as customarily manufactured. Tip 296 is shown in a magnified view.

Figure 28:
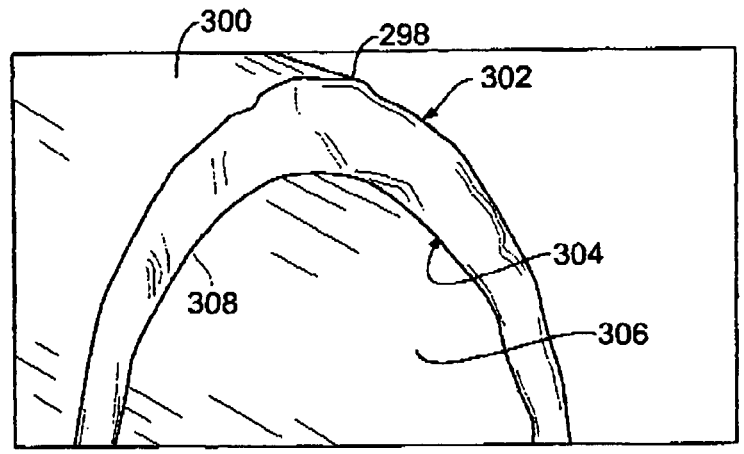
FIG. 28 is an enlarged view of FIG. 27.

A portion of lip 298 is seen in FIG. 28 in a more highly magnified view. The surface 300 of lip 298 is seen to meet tip 296 at substantially a right angle, forming a roughened edge 302. The same configuration creates a roughened edge 304, formed where lip surface 300 and tip inner surface 306 meet. Tip surface 300 is also characterized by upstanding ridges such as those identified by the numeral 308.

Edges 302 and 304, and ridges 308 are somewhat analogous to the "flashing" or "burrs" created when metallic workpieces are cut or severed. Because of the relatively thin metallic material from which phacoemulsification needles are formed, such edges and ridges are themselves thin and sharp, certainly sharp enough to snag corneal tissue when a phacoemulsification needle is inserted through a corneal incision. They are also sharp enough to damage delicate eye tissue, such as the posterior capsule, if the needle tip is brought into contact with the capsule during surgery.

I have determined that a process of rounding and highly polishing and smoothing the lips of phacoemulsification needle tips of the type described herein reduces the likelihood that delicate eye tissue will be damaged during phaco, particularly if the needle is being sued with a handpiece that produces torsional or elliptical motion.

Figure 29:
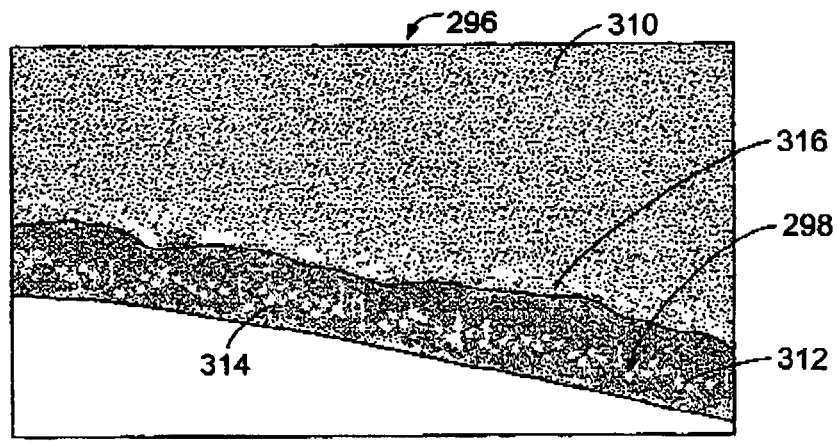
FIG. 29 is a microscopic view of a portion of the outer surface of the tip of FIGS. 27 and 28 after roughening and polishing.

Referring now to FIG. 29 the numeral 310 identifies the outer surface of tip 296 after a roughening procedure has been performed. As can be seen, surface 310 is "pitted" to create a much larger surface area for contact with tissue to be phacoemulsified.

FIG. 29 also shows a portion 312 of lip 298 after polishing. Lip surface 314 now meets outer surface 310 at a rounded edge 316, much smoother and snag-free than the roughened edge 302 shown in FIG. 28.

Figure 30:
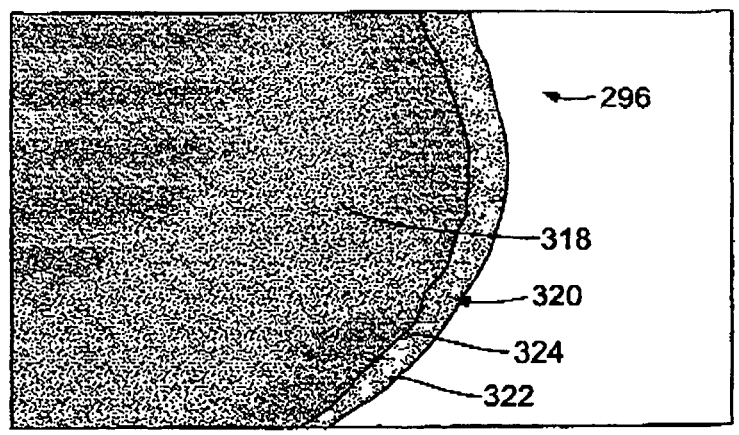
FIG. 30 is a microscopic view of a portion of the inner surface of the tip of FIGS. 27 and 28 after roughening and polishing.

In like fashion, a portion of inner surface 318 of tip 296 is shown after a roughening procedure has been performed. FIG. 30 also shows a portion 320 of lip 298 after polishing. Lip surface 322 now meets inner surface 318 at a rounded edge 324, much smoother and snag-free than the roughened edge 304 shown in FIG. 28.

The elements of surface finish are described by Quality Magazine at its website qualitymag.com as form, waviness and roughness. These elements, as they are present in the surface finish on the lips of the needles described herein, are rounded and smoothed to a degree sufficient to avoid the snagging of the tip on tissue in the eye, particularly the tissue through which the corneal incision is made and the tissue forming the capsular bag.

While the roughening procedure has been preferably described as sandblasting, other types of operations to create a controlledly roughened surface may also be used. In like fashion, other forms of polishing or smoothing devices and procedures can also be used to satisfactorily prepare the lip of each such phacoemulsification needle tip.

I claim:

1. A phacoemulsification needle for use with a phacoemulsification handpiece, said needle comprising:
    an elongate needle body having an outer surface, a cross-sectional shape, a proximal end and a distal end,
    said needle body having a central needle axis extending along its length;
    said needle body including only a single passageway extending through said needle body,
    said passageway having a uniform cross-sectional size and shape and a central axis extending along its length;
    a needle tip formed at said distal end,
    said tip having a cross-sectional shape, an exterior surface and an inner surface,
    said tip having a central longitudinal axis;
    said tip axis and said passageway axis being offset and parallel such that said tip axis and said passageway axis do not coincide;
    said exterior surface and said inner surface terminating at a lip;
    said tip having a flaring shape that flares laterally outward in the direction toward said lip and terminating at said lip;
    said tip having a mouth defined by said lip; and
    said tip cross-sectional shape being larger than said needle body cross-sectional shape.

2. The apparatus as recited in claim 1 wherein said lip is formed at an angle to a plane normal to said body axis,
    said lip having a lead portion and a trailing portion,
    said lead portion of said lip extending longitudinally past said trailing portion.

3. The apparatus as recited in claim 2 wherein said lip is formed at an angle of 30 degrees with respect to said plane.

4. The apparatus as recited in claim 2 wherein at least a part of said lead portion is substantially coextensive with said needle body outer surface.

5. The apparatus as recited in claim 2 wherein at least a part of said trailing portion is substantially coextensive with said needle body outer surface.

6. The apparatus as recited in claim 2 wherein said tip cross-sectional shape is circular.

7. The apparatus as recited in claim 2 wherein said tip cross-sectional shape is square.

8. The apparatus as recited in claim 2 wherein said passageway cross-sectional shape and said needle body cross-sectional shape are different.

9. The apparatus as recited in claim 2 wherein said tip is angled with respect to said needle body.

10. The apparatus as recited in claim 1 wherein said lip is rounded and smoothed.

11. The apparatus as recited in claim 1 wherein at least a portion of said outer surface proximate said distal end is roughened.

12. The apparatus as recited in claim 1 wherein at least a portion of said inner surface proximate said distal end is roughened.

13. The apparatus as recited in claim 1 wherein at least a portion of said outer surface proximate said distal end and at least a portion of said inner surface proximate said distal end are roughened.

14. A phacoemulsification needle for use with a phacoemulsification handpiece, said needle comprising:
    an elongate needle body having an outer surface, a cross-sectional shape, a proximal end and a distal end,
    said needle body having a central axis extending along its length;
    said needle body including only a single passageway extending through said needle body,
    said passageway having a uniform cross-sectional size and shape and a first central axis extending along its length;
    a needle tip formed at said distal end,
    said tip having a cross-sectional shape, an exterior surface and an inner surface,
    said exterior surface and said inner surface terminating at a lip;
    said tip having a central longitudinal axis;
    said tip having a flaring shape with a cross-sectional shape being larger than said needle body cross-sectional shape; and
    a bend formed on said needle body proximate said tip such that said tip axis is angled with respect to said needle body axis, and said bend formed on said needle body proximate said tip such that said passageway has a second central axis, said second central axis intersecting said first central axis of said passageway,
    at least a portion of said tip exterior surface being coextensive with that portion of said outer needle surface included in said bend, and
    at least a portion of said tip exterior surface being non-coextensive with that portion of said outer needle surface included in said bend, and
    wherein said tip axis and said second central axis of said passageway are offset one from the other such that said tip axis and said second central axis of said passageway do not coincide.

15. The apparatus as recited in claim 14 wherein said needle body axis and said first central axis of said passageway are offset one from the other such that said needle body axis and said first central axis of said passageway do not coincide.

16. The apparatus as recited in claim 14 wherein said needle body cross-sectional shape and said passageway cross-sectional shape are different.

17. The apparatus as recited in claim 14 wherein said lip is rounded and smoothed.

18. The apparatus as recited in claim 14 wherein at least a portion of said outer surface proximate said distal end is roughened.

19. The apparatus as recited in claim 14 wherein at least a portion of said inner surface proximate said distal end is roughened.

20. The apparatus as recited in claim 14 wherein at least a portion of said outer surface proximate said distal end and at least a portion of said inner surface proximate said distal end are roughened.

* * * * *